US011224737B2

(12) United States Patent
Petersen et al.

(10) Patent No.: US 11,224,737 B2
(45) Date of Patent: Jan. 18, 2022

(54) BLOOD PUMP CONTROLLERS AND METHODS OF USE FOR IMPROVED ENERGY EFFICIENCY

(71) Applicant: TC1 LLC, St. Paul, MN (US)

(72) Inventors: Ethan Petersen, Oakland, CA (US); Joseph C. Stark, San Leandro, CA (US)

(73) Assignee: TC1 LLC, St. Paul, MN (US)

( * ) Notice: Subject to any disclaimer, the term of this patent is extended or adjusted under 35 U.S.C. 154(b) by 81 days.

(21) Appl. No.: 16/893,649

(22) Filed: Jun. 5, 2020

(65) Prior Publication Data

US 2020/0297906 A1 Sep. 24, 2020

Related U.S. Application Data

(60) Division of application No. 15/908,580, filed on Feb. 28, 2018, now Pat. No. 10,722,632, which is a
(Continued)

(51) Int. Cl.
*A61M 60/871* (2021.01)
*A61M 60/50* (2021.01)
(Continued)

(52) U.S. Cl.
CPC .......... *A61M 60/871* (2021.01); *A61M 60/50* (2021.01); *H02J 1/06* (2013.01); *H02J 7/00* (2013.01); *H02J 7/0013* (2013.01); *H02J 7/0019* (2013.01); *H02J 7/0042* (2013.01); *H02J 7/0071* (2020.01); *H02J 7/0072* (2013.01); *H02J 50/12* (2016.02);
(Continued)

(58) Field of Classification Search
CPC .. A61M 2205/3317; A61M 2205/8206; A61M 2205/8243; H02J 50/12; H02J 2207/20; H02J 1/06; H02J 7/00; H02J 7/0013; H02J 7/0072; H02J 7/0042; H02J 7/025
See application file for complete search history.

(56) References Cited

U.S. PATENT DOCUMENTS 5,613,935 A 3/1997 Jarvik
5,630,836 A 5/1997 Prem et al.
(Continued)

OTHER PUBLICATIONS

Knecht et al., "High-Efficiency Transcutaneous Energy Transfer for Implantable Mechanical Heart Support Systems", IEEE Transactions on Power Electronics, vol. 30, Issue 11, Nov. 2015, pp. 6221-6236.

*Primary Examiner* — Paula J Stice
(74) *Attorney, Agent, or Firm* — Kilpatrick Townsend & Stockton LLP

(57) ABSTRACT

Methods, systems, and devices for a mechanical circulatory support system are disclosed herein. An implantable power supply can be part of a mechanical circulatory support system. The implantable power supply can include one or several energy storage components, a power source, a voltage converter, and an output bus. Power can be provided to the voltage converter from one or both of the power source and the first energy storage component. The voltage converter can convert the voltage of the power from a first voltage to a second voltage and can power the output bus.

20 Claims, 10 Drawing Sheets

Related U.S. Application Data continuation of application No. PCT/US2016/049074, filed on Aug. 26, 2016.

(60) Provisional application No. 62/211,618, filed on Aug. 28, 2015.

(51) Int. Cl.
| | |
|---|---|
| *A61M 60/40* | (2021.01) |
| *A61M 60/419* | (2021.01) |
| *H02J 50/12* | (2016.01) |
| *H02J 7/00* | (2006.01) |
| *H02J 1/06* | (2006.01) |
| *H02M 3/158* | (2006.01) |

(52) U.S. Cl.
CPC ........... *A61M 60/40* (2021.01); *A61M 60/419* (2021.01); *A61M 2205/3317* (2013.01); *A61M 2205/8206* (2013.01); *A61M 2205/8243* (2013.01); *H02J 2207/20* (2020.01); *H02M 3/158* (2013.01)

(56) References Cited

U.S. PATENT DOCUMENTS

| | | | |
|---|---|---|---|
| 5,695,471 | A | 12/1997 | Wampler |
| 5,708,346 | A | 1/1998 | Schob |
| 5,733,313 | A | 3/1998 | Barreras, Sr. et al. |
| 5,888,242 | A | 3/1999 | Antaki et al. |
| 6,053,705 | A | 4/2000 | Schob et al. |
| 6,071,093 | A | 6/2000 | Hart |
| 6,100,618 | A | 8/2000 | Schoeb et al. |
| 6,116,862 | A | 9/2000 | Rau et al. |
| 6,186,665 | B1 | 2/2001 | Maher et al. |
| 6,222,290 | B1 | 4/2001 | Schoeb et al. |
| 6,234,772 | B1 | 5/2001 | Wampler et al. |
| 6,249,067 | B1 | 6/2001 | Schob et al. |
| 6,264,635 | B1 | 7/2001 | Wampler et al. |
| 6,278,251 | B1 | 8/2001 | Schob |
| 6,351,048 | B1 | 2/2002 | Schob et al. |
| 6,355,998 | B1 | 3/2002 | Schoeb et al. |
| 6,552,511 | B1 * | 4/2003 | Fayram ............... H02J 7/0024 320/103 |
| 6,634,224 | B1 | 10/2003 | Schob et al. |
| 6,688,861 | B2 | 2/2004 | Wampler |
| 6,879,074 | B2 | 4/2005 | Amrhein et al. |
| 6,991,595 | B2 | 1/2006 | Burke et al. |
| 7,112,903 | B1 | 9/2006 | Schob |
| 7,699,586 | B2 | 4/2010 | LaRose et al. |
| 7,979,271 | B2 | 7/2011 | Bessette |
| 7,997,854 | B2 | 8/2011 | LaRose et al. |
| 8,007,254 | B2 | 8/2011 | LaRose et al. |
| 8,152,493 | B2 | 4/2012 | LaRose et al. |
| 8,323,174 | B2 | 12/2012 | Jeevanandam et al. |
| 8,449,444 | B2 | 5/2013 | Poirier |
| 8,506,471 | B2 | 8/2013 | Bourque |
| 8,562,508 | B2 | 10/2013 | Dague et al. |
| 8,588,913 | B2 | 11/2013 | Signoff et al. |
| 8,597,350 | B2 | 12/2013 | Rudser et al. |
| 8,652,024 | B1 | 2/2014 | Yanai et al. |
| 8,657,733 | B2 | 2/2014 | Ayre et al. |
| 8,668,473 | B2 | 3/2014 | LaRose et al. |
| 2005/0071001 | A1 | 3/2005 | Jarvik |
| 2007/0078293 | A1 | 4/2007 | Shambaugh et al. |
| 2008/0021394 | A1 | 1/2008 | Larose et al. |
| 2009/0203957 | A1 | 8/2009 | Larose et al. |
| 2010/0305692 | A1 | 12/2010 | Thomas et al. |
| 2011/0060281 | A1 | 3/2011 | Aeschlimann et al. |
| 2011/0101790 | A1 | 5/2011 | Budgett |
| 2011/0160516 | A1 | 6/2011 | Dague et al. |
| 2012/0046514 | A1 | 2/2012 | Bourque |
| 2012/0095281 | A1 | 4/2012 | Reichenbach et al. |
| 2012/0157755 | A1 | 6/2012 | D'Ambrosio |
| 2013/0009609 | A1 | 1/2013 | Andersen et al. |
| 2013/0096364 | A1 | 4/2013 | Reichenbach et al. |
| 2013/0121821 | A1 | 5/2013 | Ozaki et al. |
| 2013/0127253 | A1 | 5/2013 | Stark et al. |
| 2013/0170970 | A1 | 7/2013 | Ozaki et al. |
| 2013/0225909 | A1 | 8/2013 | Dormanen et al. |
| 2013/0314047 | A1 | 11/2013 | Eagle et al. |
| 2014/0378742 | A1 | 12/2014 | Badstibner et al. |
| 2015/0290373 | A1 | 10/2015 | Rudser et al. |
| 2015/0290374 | A1 | 10/2015 | Bourque et al. |
| 2015/0381176 | A1 | 12/2015 | Schie et al. |

* cited by examiner

BLOOD PUMP CONTROLLERS AND METHODS OF USE FOR IMPROVED ENERGY EFFICIENCY

CROSS-REFERENCES TO RELATED APPLICATIONS

The present application is a Divisional of U.S. patent application Ser. No. 15/908,580 filed Feb. 28, 2018 (Allowed); which is a Continuation of PCT Appln No. PCT/US2016/049074 filed Aug. 26, 2016; which claims priority to U.S. Provisional Appln No. 62/211,618 filed Aug. 28, 2015, the disclosures of which are incorporated herein by reference in their entirety for all purposes.

BACKGROUND

Ventricular assist devices, known as VADs, are implantable blood pumps used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

A patient suffering from heart failure, also called congestive heart failure, may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

While a VAD can greatly improve the quality of a patient's life, the consequences of insufficient power for proper operation of the VAD are significant to patient safety. To minimize the risk of lack of power, VADs are frequently used in connection with powering systems that may be tied to one or several batteries or to the power grid. While these systems are able to reliably provide power to the VAD, they can be bulky, cumbersome, and, in many cases, inefficient. Thus, improvements in the systems and methods for providing power to the VAD are desired.

BRIEF SUMMARY

The present invention provides improved systems, methods, and devices which can increase the efficiency and reliability of powering an implantable blood pump. For example, an implantable power supply can include multiple redundant power pathways via which the implantable blood pump can be powered. The implantable power supply can further include a power source connected to an input bus having a higher voltage than an output bus. This higher voltage of the input bus can improve the efficiency of power transfer to the implantable power source. It will further be appreciated that such improved power supply systems are not limited to implantable power supply systems but can also find application to external power supply systems such as external blood pump controllers that are positioned outside the body.

Embodiments of the present disclosure relate to a mechanical circulatory support system. The mechanical circulatory support system can include an implantable blood pump, and an implantable power supply that can electrically power the implantable blood pump. The implantable power supply can include a first power pathway to the implantable blood pump, a second power pathway to the implantable blood pump, wherein the second power pathway can be redundant to the first power pathway, a first energy storage component, and a second energy storage component. In some embodiments, the first and second energy storage components are arranged in series. It is of particular advantage to provide parallel power pathways and/or configuration of the first and second energy storage components in series to increase the reliability with which the implantable blood pump is powered. In some embodiments, the mechanical circulatory support system can include a non-implantable, external charger that can supply electrical power to the implantable power supply, for example via transcutaneous energy transfer or alternatively via a hard driveline connection.

In some embodiments of the mechanical circulatory support system, the implantable power supply further includes an input bus having a first voltage, and a voltage converter connected to the input bus that can output a second voltage to the implantable blood pump. In some embodiments, the implantable power supply further includes a power source that can receive electrical power from the external charger and provide power to the input bus. In some embodiments, the non-implantable charger can be configured for transcutaneous energy transfer.

In some embodiments of the mechanical circulatory support system, the non-implantable charger includes a first energy storage feature, a second energy storage feature, wherein the first and second energy storage features are arranged in series, and a second voltage converter. In some embodiments, the second voltage converter can be a boost converter. In some embodiments, the boost converter can double the voltage of at least one of the first energy storage feature or the second energy storage feature.

In some embodiments of the mechanical circulatory support system, the non-implantable charger further comprises a transcutaneous energy transfer system (TETS) transmitter. In some embodiments, the power source can be a TETS receiver. In some embodiments, the first power pathway connects the power source to the implantable blood pump via the input bus and the voltage converter, and the second power pathway connects the first energy storage component to the implantable blood pump via input the bus and the voltage converter. The present invention may find particular advantages in a fully implanted blood pump system. For example, the voltage converter can enable the operation of the input bus at a higher voltage than the voltage of the output bus. This higher voltage of the input bus increases the power throughput of the TETS power transfer.

In some embodiments of the mechanical circulatory support system, the voltage converter can be a buck or boost converter, and in some embodiments, the voltage converter can be a flyback converter. In some embodiments, the implantable power supply can include a third power pathway to the implantable blood pump, wherein the third power pathway can be redundant to the first and second power pathways. In some embodiments, the third power pathway connects the second energy storage component to the implantable blood pump. In some embodiments, the third power pathway excludes the input bus and the voltage converter.

In some embodiments of the mechanical circulatory support system, the first energy storage component has a first voltage, and the second energy storage component has a second voltage. In some embodiments, the first and second voltages are equal, and in some embodiments, the first voltage is different than the second voltage.

Embodiments of the present disclosure relate to an implantable power supply that can electrically power an implantable blood pump. The implantable power supply can include a first energy storage component, a second energy storage component, wherein the first and second energy storage components are arranged in series, an output bus directly electrically connected to the second energy storage component, and a voltage converter. In some embodiments, the voltage converter electrically connects the first energy storage component to the output bus.

In some embodiments, the implantable power supply is electrically connectable to the implantable blood pump via the output bus. In some embodiments, the second energy storage component is electrically connected to the output bus such that the voltage of the output bus matches the voltage of the second energy storage component. In some embodiments, the implantable power supply further includes an input bus, and a power source. In some embodiments, the power source is connected to the output bus via the voltage converter. In some embodiments, the first energy storage component is electrically connected to the input bus such that the voltage of the input bus matches the sum of the voltages of the first and second energy storage components.

In some embodiments of the implantable power supply, the power source can be a TETS receiver. In some embodiments, the TETS receiver can couple with a TETS transmitter to receive power from a non-implantable charger. In some embodiments, the TETS receiver and/or transmitter can be an inductive coil.

In some embodiments of the implantable power supply, the voltage converter comprises a buck converter. In some embodiments, the first energy storage component can be a first battery, and the second energy storage component can be a second battery. In some embodiments, the first battery can have a first number of cells, and the second battery can have a second number of cells. In some embodiments, the first number of cells can be different than the second number of cells.

Embodiments of the present disclosure relate to a method of powering an implantable blood pump. In some embodiments, the power device can electrically power an implantable blood pump. The method includes powering an input bus having a first voltage, which input bus is connected to a power source and a first energy storage component, and which input bus is powered by at least one of: the power source; and the first energy storage component. The method can include converting from the first voltage to a second voltage via a voltage converter, which voltage converter is electrically connected to the input bus. The method can include powering an output bus having the second voltage, which output bus is electrically connected with the voltage converter and a second energy storage component. In some embodiments, the output bus is powered by at least one of the voltage converter and the second energy storage component, and in some embodiments the first and second energy storage components are arranged in series.

In some embodiments, the method can include charging at least one of the first and second energy storage components, and in some embodiments, the method can include discharging at least one of the first and second energy storage components. In some embodiments, the input bus is only powered by the first energy storage component. In some embodiments, the powering of the input bus is inadequate to power the implantable blood pump. In some embodiments, the power source can be a transcutaneous energy transfer system (TETS) receiver. In some embodiments, the method can include transmitting power from a non-implantable charger to the power source of the implantable power device. In some embodiments, the non-implantable charger can include a transcutaneous energy transfer system (TETS) transmitter. In some embodiments, at least one of: the TETS receiver; and the TETS transmitter is an inductive coil.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION

Figure 1A:
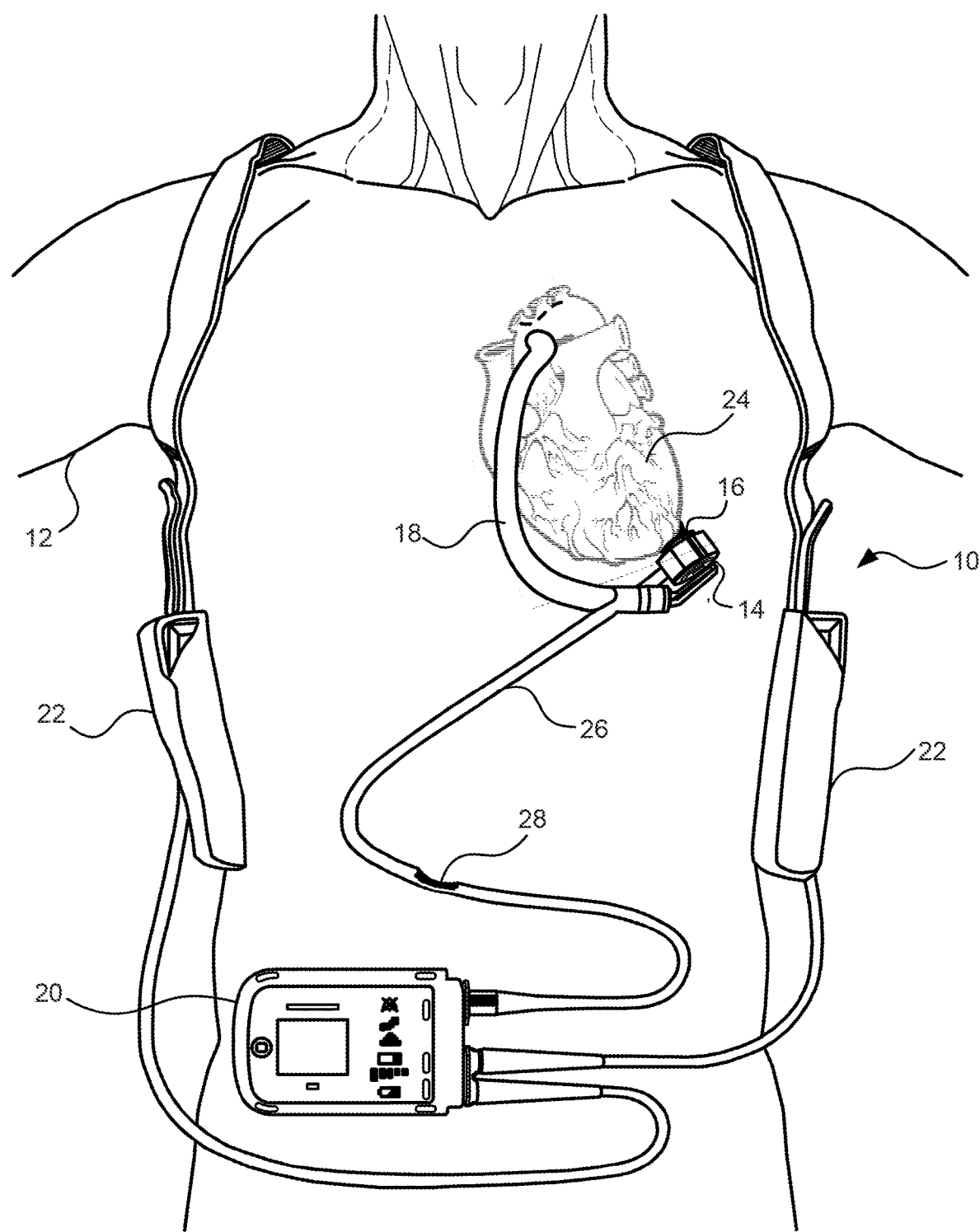
FIG. 1A is an illustration of a mechanical circulatory support system implanted in a patient's body.

FIG. 1A is an illustration of a mechanical circulatory support system 10 implanted in a patient's body 12. The mechanical circulatory support system 10 comprises an implantable blood pump 14, ventricular cuff 16, outflow cannula 18, system controller 20, and external power sources 22. The implantable blood pump 14 may comprise a VAD that is attached to an apex of the left ventricle, as illustrated, or the right ventricle, or both ventricles of the heart 24. The VAD may comprise a centrifugal (as shown) or axial flow pump as described in further detail herein that is capable of pumping the entire output delivered to the left ventricle from the pulmonary circulation (i.e., up to 10 liters per minute). Related blood pumps applicable to the present invention are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, 8,668,473, 8,419,609, 7,976,271, 8,852,072, 9,091,271, 9,265,870, 8,864,643, 9,382,908, 9,068,572, 8,882,744, all of which are incorporated herein by reference for all purposes in their entirety. With reference to FIGS. 1 and 2, the blood pump 14 may be attached to the heart 24 via the ventricular cuff 16 which is sewn to the heart 24 and coupled to the blood pump 14. The other end of the blood pump 14 connects to the ascending aorta via the outflow cannula 18 so that the VAD effectively diverts blood from the weakened ventricle and propels it to the aorta for circulation to the rest of the patient's vascular system.

FIG. 1A illustrates the mechanical circulatory support system 10 during external power source 22 powered operation. A driveline 26 which exits through the patient's abdomen 28, connects the implanted blood pump 14 to the system controller 20, which monitors system 10 operation. Related controller systems applicable to the present invention are described in greater detail below and in U.S. Pat. Nos. 5,888,242, 6,991,595, 8,323,174, 8,449,444, 8,506, 471, 8,597,350, and 8,657,733 and U.S. Patent Publication Nos. 2005/0071001 and 2013/0314047, all of which are incorporated herein by reference for all purposes in their entirety. The system may be powered by either one, two, or more external power sources 22. It will be appreciated that although the system controller 20 and power source 22 are illustrated outside/external to the patient body, the driveline 26, system controller 20 and/or power source 22 may be partially or fully implantable within the patient, as separate components or integrated with the blood bump 14. Examples of such modifications are further described in U.S. Pat. No. 8,562,508 and U.S. Patent Publication No. 2013/0127253, all of which are incorporated herein by reference for all purposes in their entirety.

Figure 1B:
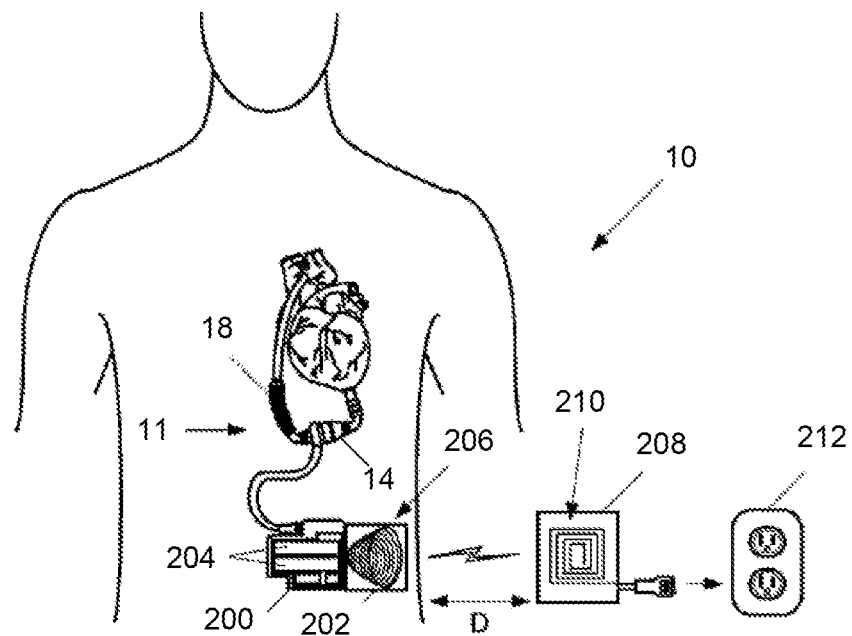
FIG. 1B is an illustration of one embodiment of a mechanical circulatory support system with a Transcutaneous Energy Transfer System (TETS) implanted in a patient's body in a first position.
Figure 1C:
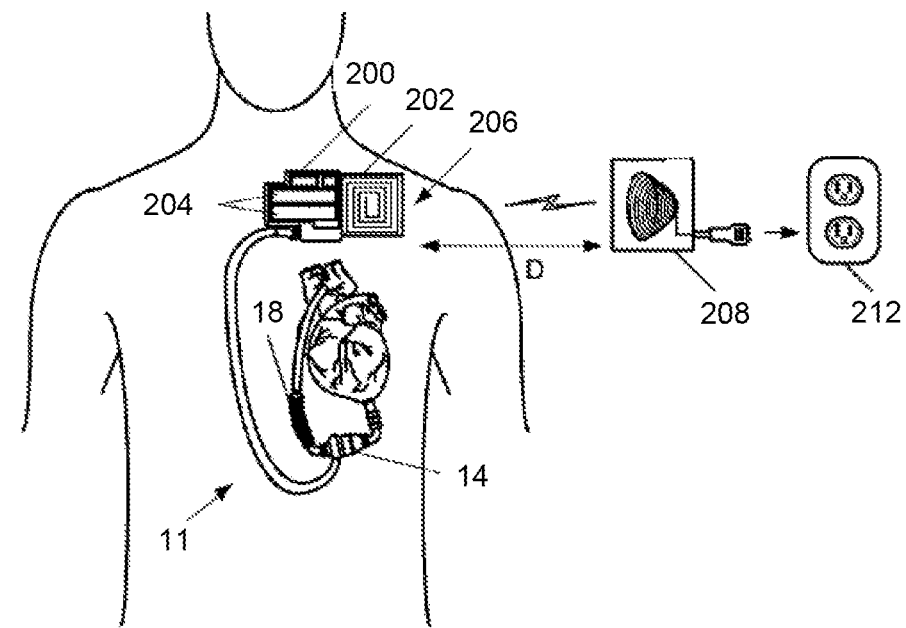
FIG. 1C is an illustration of one embodiment of a mechanical circulatory support system with a Transcutaneous Energy Transfer System (TETS) implanted in a patient's body in a second position.
Figure 2:
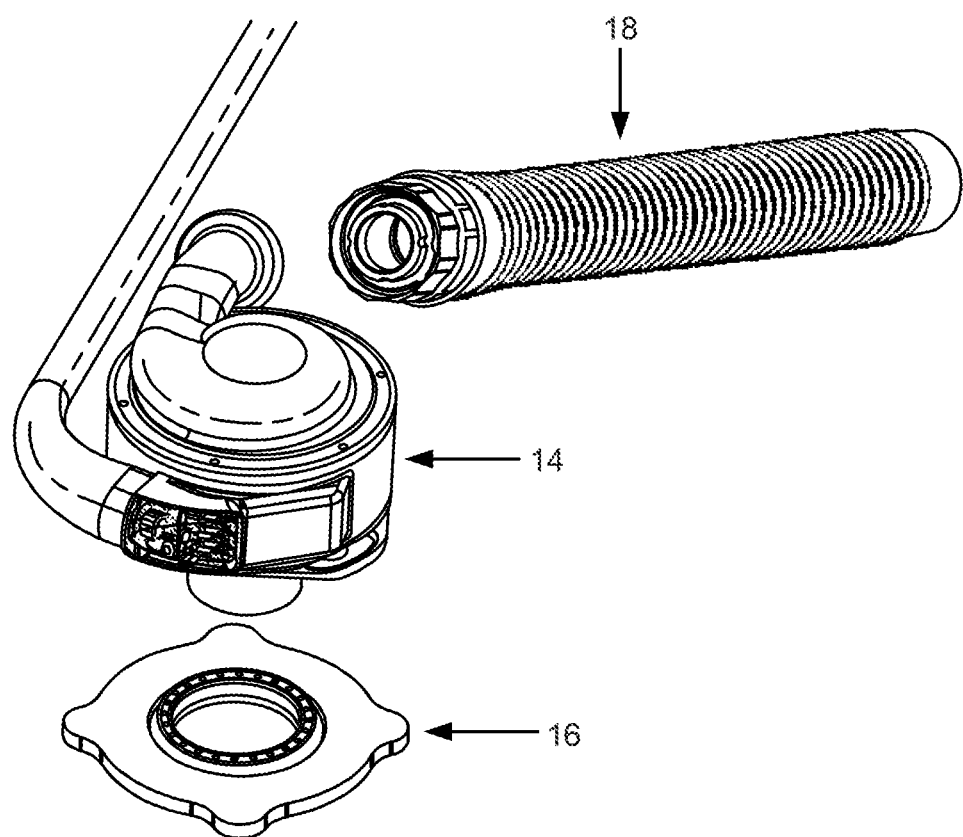
FIG. 2 is an exploded view of certain components of the circulatory support system that are implanted in a patient's body.

FIGS. 1B and 1C illustrates exemplary embodiments of the mechanical circulatory support system 10 with internal components 11 according to embodiments of the present invention. The internal components 11 include a cannula 18, a blood pump 14, a rechargeable power storage device 200, also referred to herein as an implantable power supply 200, and a power receiver unit 202. The rechargeable power storage device 200 may include two or more energy storage components 204, which can be, for example, batteries including rechargeable batteries, capacitors, fuel cells, or the like. In some embodiments, these energy storage components 204 can include a first energy storage component and a second energy storage component. In some embodiments, the first and second energy storage components can be matched, and in other embodiments, the first and second energy storage components can be unmatched. In some embodiments, for example, the first and second energy storage components can have the same voltages and/or the same number of cells, and in some embodiments, the first and second energy storage components can have different voltages and/or different numbers of cells.

The rechargeable power storage device 200 can be implanted in a location away from the cannula 18, for example, in the lower abdominal as shown in FIG. 1B. The power receiving unit 202 includes a TETS receiver 206 that can be, for example, a receiver, a resonator, and inductive coil or the like, that can be coupled to the power storage device 200, which is the electrical load of the power receiver unit 202. The resonant frequency of the TETS receiver 206 can be, for example, in a range of 100 kHz to 10 MHz. In an exemplary embodiment, the resonant frequency of the receiver resonator 206 can be 100 kHz, 500 kHz, 1 MHz, or 10 MHz. In other embodiments, another resonant frequency that is safe for the human body can be used.

The mechanical circulatory support system 10 also includes a power transmitter unit 208, also referred to herein as a non-implantable charger 208 that is external to the patient. The transmitter unit 208 includes a transmitter resonator 210, also referred to herein as a TETS transmitter 210. The transmitter resonator 210 can include, for example, a coil, including an inductive coil that is configured to be coupled to an electric power source 212 such as an electrical wall outlet or external power sources 22. When the transmitter unit 208 is powered by, for example, connection to the electric power source 212, an electrical current is generated in the coil of the transmitter resonator 210. The resonant frequency of the transmitter resonator 210 can be in a range of 100 kHz to 10 MHz. In an exemplary embodiment, the resonant frequency of the transmitter resonator 210 can be 100 kHz, 500 kHz, 1 MHz, or 10 MHz. In other embodiments, another resonant frequency that is safe for the human body can be used.

The transmitter resonator 210 as part of the transmitter unit 208 may be embedded in a stationary object such as a wall, a chair, a bed, or other fixtures such as a car seat or objects that do not move by themselves without external control or human assistance. The source of power for a stationary and embedded transmitter resonator is generally alternating current from an electric outlet, but can also be direct current from a battery source. In other embodiments, the transmitter resonator 210 may be part of a piece of wearable clothing such as a vest or a jacket, or other wearable accessories. In the case of a transmitter resonator that is embedded into a piece of clothing or object wearable by a person that moves with a person, the source of power would be portable sized rechargeable batteries that also could be worn by the patient.

When the receiver unit 202 in the patient comes within a separation distance D of the transmitter unit 208, the mechanical circulatory support system 10 is able to wirelessly transfer energy from the transmitter unit 208 to the receiver unit 202 to recharge the power storage device 200 of the internal components 11. In one embodiment, at a given separation distance D being in the range of 2.5 cm to 35 cm, the transmitter unit 208 is able to deliver power in the range of 5 W to 20 W to the receiver unit 202 to recharge the batteries 204 in the power storage device 200 of the internal components 11.

Figure 3:
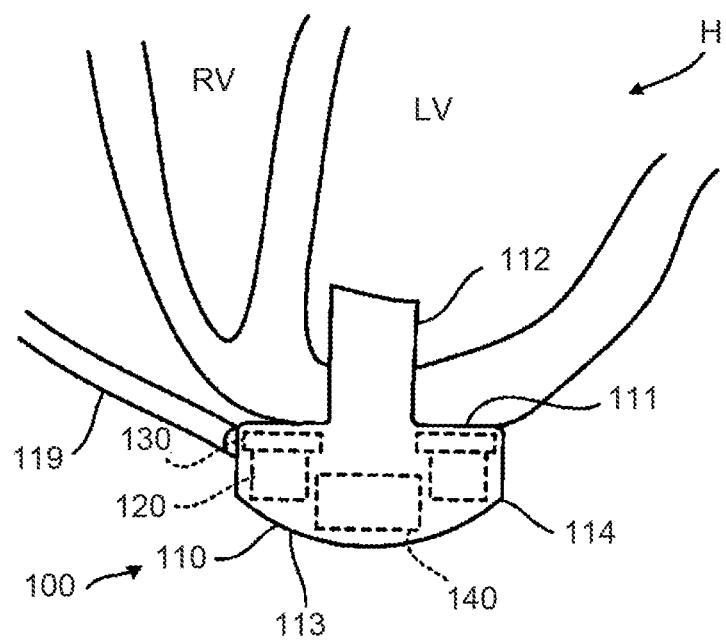
FIG. 3 is an illustration of a blood pump in an operational position implanted in a patient's body.
Figure 4:
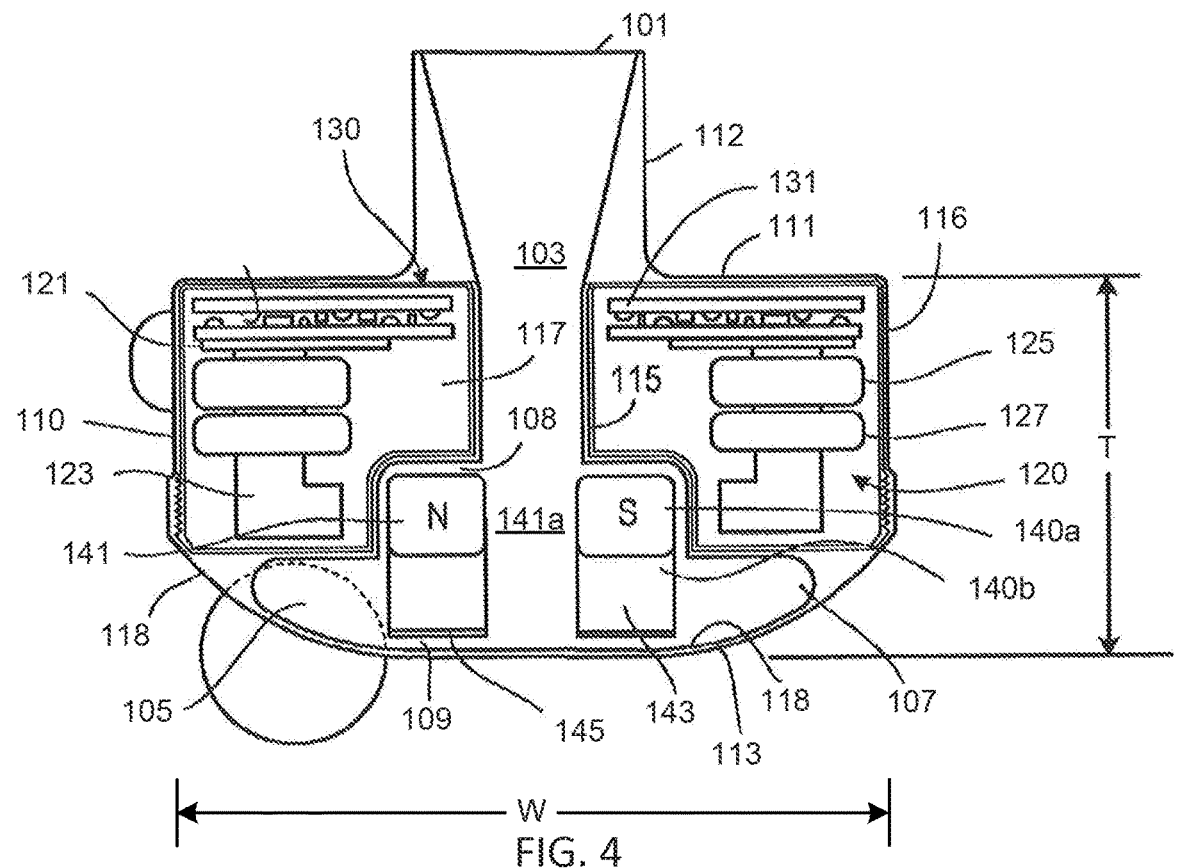
FIG. 4 is a cross-sectional view of the blood pump of FIG. 3.
Figure 5:
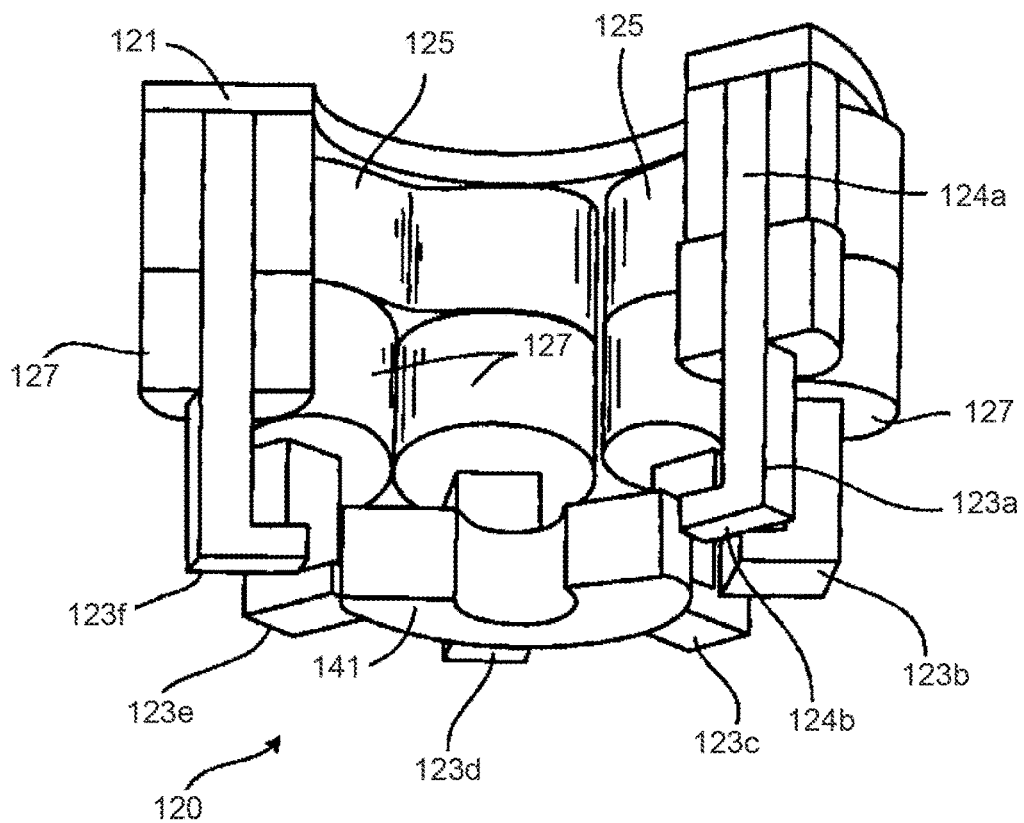
FIG. 5 is a partial cut-away perspective view of a stator of a blood pump.

With reference to FIGS. 3 to 5, a left ventricular assist blood pump 100 having a circular shaped housing 110 is implanted in a patient's body with a first face 111 of the housing 110 positioned against the patient's heart H and a second face 113 of the housing 110 facing away from the heart H. The first face 111 of the housing 110 includes an inlet cannula 112 extending into the left ventricle LV of the heart H. The second face 113 of the housing 110 has a chamfered edge 114 to avoid irritating other tissue that may come into contact with the blood pump 100, such as the patient's diaphragm. To construct the illustrated shape of the puck-shaped housing 110 in a compact form, a stator 120 and electronics 130 of the pump 100 are positioned on the inflow side of the housing toward first face 111, and a rotor 140 of the pump 100 is positioned along the second face 113. This positioning of the stator 120, electronics 130, and rotor 140 permits the edge 114 to be chamfered along the contour of the rotor 140, as illustrated in at least FIGS. 2-4, for example.

Referring to FIG. 4, the blood pump 100 includes a dividing wall 115 within the housing 110 defining a blood flow conduit 103. The blood flow conduit 103 extends from an inlet opening 101 of the inlet cannula 112 through the stator 120 to an outlet opening 105 defined by the housing 110. The rotor 140 is positioned within the blood flow conduit 103. The stator 120 is disposed circumferentially about a first portion 140a of the rotor 140, for example about a permanent magnet 141. The stator 120 is also positioned relative to the rotor 140 such that, in use, blood flows within the blood flow conduit 103 through the stator 120 before reaching the rotor 140. The permanent magnet 141 has a permanent magnetic north pole N and a permanent magnetic south pole S for combined active and passive magnetic levitation of the rotor 140 and for rotation of the rotor 140. The rotor 140 also has a second portion 140b that includes impeller blades 143. The impeller blades 143 are located within a volute 107 of the blood flow conduit such that the impeller blades 143 are located proximate to the second face 113 of the housing 110.

The puck-shaped housing 110 further includes a peripheral wall 116 that extends between the first face 111 and a removable cap 118. As illustrated, the peripheral wall 116 is formed as a hollow circular cylinder having a width W between opposing portions of the peripheral wall 116. The housing 110 also has a thickness T between the first face 111 and the second face 113 that is less than the width W. The thickness T is from about 0.5 inches to about 1.5 inches, and the width W is from about 1 inch to about 4 inches. For example, the width W can be approximately 2 inches, and the thickness T can be approximately 1 inch.

The peripheral wall 116 encloses an internal compartment 117 that surrounds the dividing wall 115 and the blood flow conduit 103, with the stator 120 and the electronics 130 disposed in the internal compartment 117 about the dividing wall 115. The removable cap 118 includes the second face 113, the chamfered edge 114, and defines the outlet opening 105. The cap 118 can be threadedly engaged with the peripheral wall 116 to seal the cap 118 in engagement with the peripheral wall 116. The cap 118 includes an inner surface 118a of the cap 118 that defines the volute 107 that is in fluid communication with the outlet opening 105.

Within the internal compartment 117, the electronics 130 are positioned adjacent to the first face 111 and the stator 120 is positioned adjacent to the electronics 130 on an opposite side of the electronics 130 from the first face 111. The electronics 130 include circuit boards 131 and various components carried on the circuit boards 131 to control the operation of the pump 100 (e.g., magnetic levitation and/or drive of the rotor) by controlling the electrical supply to the stator 120. The housing 110 is configured to receive the circuit boards 131 within the internal compartment 117 generally parallel to the first face 111 for efficient use of the space within the internal compartment 117. The circuit boards also extend radially-inward towards the dividing wall 115 and radially-outward towards the peripheral wall 116. For example, the internal compartment 117 is generally sized no larger than necessary to accommodate the circuit boards 131, and space for heat dissipation, material expansion, potting materials, and/or other elements used in installing the circuit boards 131. Thus, the external shape of the housing 110 proximate the first face 111 generally fits the shape of the circuits boards 131 closely to provide external dimensions that are not much greater than the dimensions of the circuit boards 131.

With continued reference to FIGS. 4 and 5, the stator 120 includes a back iron 121 and pole pieces 123a-123f arranged at intervals around the dividing wall 115. The back iron 121 extends around the dividing wall 115 and is formed as a generally flat disc of a ferromagnetic material, such as steel, in order to conduct magnetic flux. The back iron 121 is arranged beside the control electronics 130 and provides a base for the pole pieces 123a-123f.

Each of the pole piece 123a-123f is L-shaped and has a drive coil 125 for generating an electromagnetic field to rotate the rotor 140. For example, the pole piece 123a has a first leg 124a that contacts the back iron 121 and extends from the back iron 121 towards the second face 113. The pole piece 123a may also have a second leg 124b that extends from the first leg 124a through an opening of a circuit board 131 towards the dividing wall 115 proximate the location of the permanent magnet 141 of the rotor 140. In an aspect, each of the second legs 124b of the pole pieces 123a-123f is sticking through an opening of the circuit board 131. In an aspect, each of the first legs 124a of the pole pieces 123a-123f is sticking through an opening of the circuit board 131. In an aspect, the openings of the circuit board are enclosing the first legs 124a of the pole pieces 123a-123f.

In a general aspect, the implantable blood pump 100 may include a Hall sensor that may provide an output voltage, which is directly proportional to a strength of a magnetic field that is located in between at least one of the pole pieces 123a-123f and the permanent magnet 141, and the output voltage may provide feedback to the control electronics 130 of the pump 100 to determine if the rotor 140 and/or the permanent magnet 141 is not at its intended position for the operation of the pump 100. For example, a position of the rotor 140 and/or the permanent magnet 141 may be adjusted, e.g. the rotor 140 or the permanent magnet 141 may be pushed or pulled towards a center of the blood flow conduit 103 or towards a center of the stator 120.

Each of the pole pieces 123a-123f also has a levitation coil 127 for generating an electromagnetic field to control the radial position of the rotor 140. Each of the drive coils 125 and the levitation coils 127 includes multiple windings of a conductor around the pole pieces 123a-123f. Particularly, each of the drive coils 125 is wound around two adjacent ones of the pole pieces 123, such as pole pieces 123d and 123e, and each levitation coil 127 is wound around a single pole piece. The drive coils 125 and the levitation coils 127 are wound around the first legs of the pole pieces 123, and magnetic flux generated by passing electrical current though the coils 125 and 127 during use is conducted through the first legs and the second legs of the pole pieces 123 and the back iron 121. The drive coils 125 and the levitation coils 127 of the stator 120 are arranged in opposing pairs and are controlled to drive the rotor and to radially levitate the rotor 140 by generating electromagnetic fields that interact with the permanent magnetic poles S and N of the permanent magnet 141. Because the stator 120 includes both the drive coils 125 and the levitation coils 127, only a single stator is needed to levitate the rotor 140 using only passive and active magnetic forces. The permanent magnet 141 in this configuration has only one magnetic moment and is formed from a monolithic permanent magnetic body 141. For example, the stator 120 can be controlled as discussed in U.S. Pat. No. 6,351,048, the entire contents of which are incorporated herein by reference for all purposes. The control electronics 130 and the stator 120 receive electrical power from a remote power supply via a cable 119 (FIG. 3). Further related patents, namely U.S. Pat. Nos. 5,708,346, 6,053,705, 6,100,618, 6,222,290, 6,249,067, 6,278,251, 6,351,048, 6,355,998, 6,634,224, 6,879,074, and 7,112,903, all of which are incorporated herein by reference for all purposes in their entirety.

The rotor 140 is arranged within the housing 110 such that its permanent magnet 141 is located upstream of impeller blades in a location closer to the inlet opening 101. The permanent magnet 141 is received within the blood flow conduit 103 proximate the second legs 124b of the pole pieces 123 to provide the passive axial centering force though interaction of the permanent magnet 141 and ferromagnetic material of the pole pieces 123. The permanent magnet 141 of the rotor 140 and the dividing wall 115 form a gap 108 between the permanent magnet 141 and the dividing wall 115 when the rotor 140 is centered within the dividing wall 115. The gap 108 may be from about 0.2 millimeters to about 2 millimeters. For example, the gap 108 is approximately 1 millimeter. The north permanent magnetic pole N and the south permanent magnetic pole S of the permanent magnet 141 provide a permanent magnetic attractive force between the rotor 140 and the stator 120 that acts as a passive axial centering force that tends to maintain the rotor 140 generally centered within the stator 120 and tends to resist the rotor 140 from moving towards the first face 111 or towards the second face 113. When the gap 108 is smaller, the magnetic attractive force between the permanent magnet 141 and the stator 120 is greater, and the gap 108 is sized to allow the permanent magnet 141 to provide the passive magnetic axial centering force having a magnitude that is adequate to limit the rotor 140 from contacting the dividing wall 115 or the inner surface 118a of the cap 118. The rotor 140 also includes a shroud 145 that covers the ends of the impeller blades 143 facing the second face 113 that assists in directing blood flow into the volute 107. The shroud 145 and the inner surface 118a of the cap 118 form a gap 109 between the shroud 145 and the inner surface 118a when the rotor 140 is levitated by the stator 120. The gap 109 is from about 0.2 millimeters to about 2 millimeters. For example, the gap 109 is approximately 1 millimeter.

As blood flows through the blood flow conduit 103, blood flows through a central aperture 141a formed through the permanent magnet 141. Blood also flows through the gap 108 between the rotor 140 and the dividing wall 115 and through the gap 109 between the shroud 145 and the inner surface 108a of the cap 118. The gaps 108 and 109 are large enough to allow adequate blood flow to limit clot formation that may occur if the blood is allowed to become stagnant. The gaps 108 and 109 are also large enough to limit pressure forces on the blood cells such that the blood is not damaged when flowing through the pump 100. As a result of the size of the gaps 108 and 109 limiting pressure forces on the blood cells, the gaps 108 and 109 are too large to provide a meaningful hydrodynamic suspension effect. That is to say, the blood does not act as a bearing within the gaps 108 and 109, and the rotor is only magnetically-levitated. In various embodiments, the gaps 108 and 109 are sized and dimensioned so the blood flowing through the gaps forms a film that provides a hydrodynamic suspension effect. In this manner, the rotor can be suspended by magnetic forces, hydrodynamic forces, or both.

Because the rotor 140 is radially suspended by active control of the levitation coils 127 as discussed above, and because the rotor 140 is axially suspended by passive interaction of the permanent magnet 141 and the stator 120, no rotor levitation components are needed proximate the second face 113. The incorporation of all the components for rotor levitation in the stator 120 (i.e., the levitation coils 127 and the pole pieces 123) allows the cap 118 to be contoured to the shape of the impeller blades 143 and the volute 107. Additionally, incorporation of all the rotor levitation components in the stator 120 eliminates the need for electrical connectors extending from the compartment 117 to the cap 118, which allows the cap to be easily installed and/or removed and eliminates potential sources of pump failure.

In use, the drive coils 125 of the stator 120 generates electromagnetic fields through the pole pieces 123 that selectively attract and repel the magnetic north pole N and the magnetic south pole S of the rotor 140 to cause the rotor 140 to rotate within stator 120. For example, the Hall sensor may sense a current position of the rotor 140 and/or the permanent magnet 141, wherein the output voltage of the Hall sensor may be used to selectively attract and repel the magnetic north pole N and the magnetic south pole S of the rotor 140 to cause the rotor 140 to rotate within stator 120. As the rotor 140 rotates, the impeller blades 143 force blood into the volute 107 such that blood is forced out of the outlet opening 105. Additionally, the rotor draws blood into pump 100 through the inlet opening 101. As blood is drawn into the blood pump by rotation of the impeller blades 143 of the rotor 140, the blood flows through the inlet opening 101 and flows through the control electronics 130 and the stator 120 toward the rotor 140. Blood flows through the aperture 141a of the permanent magnet 141 and between the impeller blades 143, the shroud 145, and the permanent magnet 141, and into the volute 107. Blood also flows around the rotor 140, through the gap 108 and through the gap 109 between the shroud 145 and the inner surface 118a of the cap 118. The blood exits the volute 107 through the outlet opening 105, which may be coupled to an outflow cannula.

Figure 6:
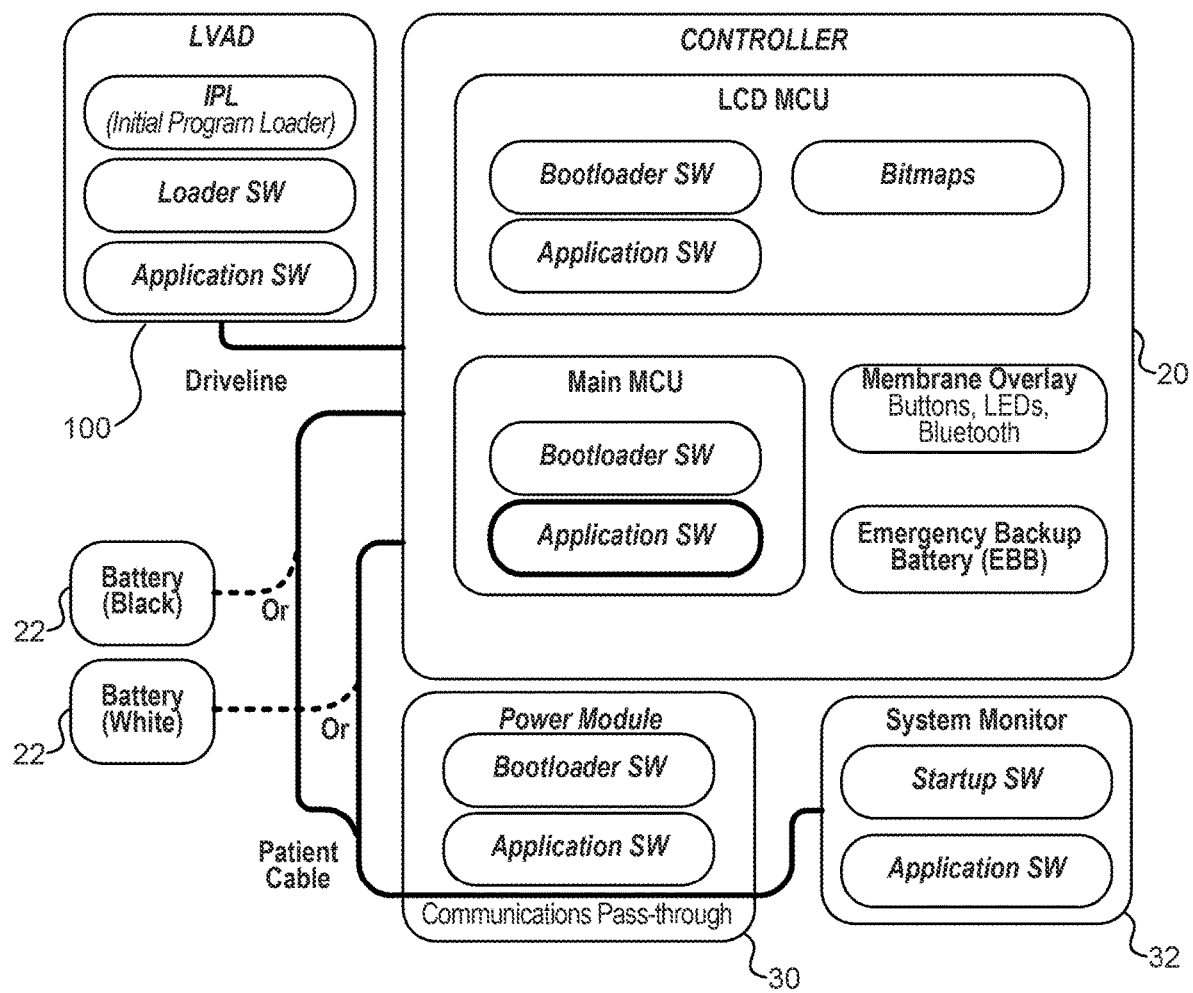
FIG. 6 is a schematic diagram of an overall communication architecture of the mechanical support system of FIG. 1A.

FIG. 6 is a schematic diagram of an overall communication architecture of the mechanical support system of FIG. 1A. A driveline couples the implanted blood pump 100 to the system controller 20, which monitors system operation via various software applications. The blood pump 100 itself also includes several software applications that are executable by the on board electronics 130 (e.g., processors) for various functions, such as to control radial levitation and/or drive of the rotor of the pump 100 during operation. The system controller 20 may in turn be coupled to external power sources 22 or a power module 30 that connect to an AC electrical outlet. The system controller 20 may also include an emergency backup battery (EBB) to power the system (e.g., when the external power sources 22 are depleted) and a membrane overlay, including bluetooth capabilities for wireless data communication. An external computer having a system monitor 32 that is configurable by an operator, such as clinician or patient, may further be coupled to the circulatory support system for configuring the system controller 20, implanted blood pump 100, and/or patient parameters, updating software on the system controller 20 and/or implanted blood pump 100, monitoring system operation, and/or as a conduit for system inputs or outputs.

In some embodiments, the software applications of the blood pump 100 can include, for example, an initial program loader (IPL), loader software, and/or application software. In some embodiments, the IPL can be configured to select and load one or several software applications corresponding to one or several modes of operation of the blood pump 100. In some embodiments, these one or several modes of operation of the blood pump 100 can include an operation mode, a test mode, a fault mode, or the like. The selecting and loading of one or several software applications corresponding to one or several modes of operation of the blood pump 100 can include, for example, selecting and loading one or several of the loader software and/or the application software. In some embodiments, the IPL can include information relating to one or several failsafe and/or fault protocols that can be used by the blood pump 100. Some of these failsafe and/or fault protocols will be discussed at length below.

The loader software, can, in some embodiments, be configured to direct the operation of the blood pump 100 during the loading of one or several software applications onto the blood pump 100. This direction of the operation of the blood pump 100 during loading of one or several software applications can include, for example, directing the blood pump 100 to stop operation during the loading of the one or several software applications or directing the blood pump 100 to continue operation during the loading of the one or several software applications according to a previously received software application. These one or several software applications can include, for example, one or several application softwares, one or several IPL applications, or the like. In some embodiments, the loader software can prescribe one or several processes for updating and/or loading one or several software applications onto the blood pump 100. These processes and associated failsafes will be discussed in greater details below.

The application software can include one or several parameters for directing the pumping operation of the blood pump 100. In some embodiments, the application software can comprise one of a clinical application software which can be configured to control the operation of the blood pump 100 when implanted in a patient, and in some embodiments, the application software can comprise a production software that can be configured to control the operation of the blood pump 100 during production and/or testing of the blood pump 100.

In some embodiments, these parameters can specify a control or control regimen for the position and/or motion of the rotor 140. For example, these parameters can specify the aspects of the levitation control and/or rotation control of the rotor 140.

In some embodiments, the parameters of the application software can specify, for example a desired performance of the blood pump 100 and/or one or several desired performance parameters, such as, for example, a desired pump speed, and desired pumped flow rate, a pulse generation, or the like. In some embodiments, these parameters can be actively used to control the operation of the blood pump 100, and in some embodiments these parameters can be stored during normal operation of the blood pump 100 and used as part of one or several failsafe and/or fault protocols. In some embodiments, the parameters of the application software can specify the generation and/or collection of data from the blood pump 100 and/or interfacing of the blood pump 100 to other components of the mechanical circulatory support system 10.

In some embodiments, the application software can comprises a first application software containing parameters relating to the current operation of the blood pump, and in some embodiments, the application software can comprise a second application software containing parameters unrelated to the current operation of the blood pump 100. In one embodiment, for example, the blood pump 100 can comprise the second application software as a backup to the first application software. In some embodiments, the first application software can be identical to the second application software, and in some embodiments, the first application can be different than the second application software.

Figure 7:
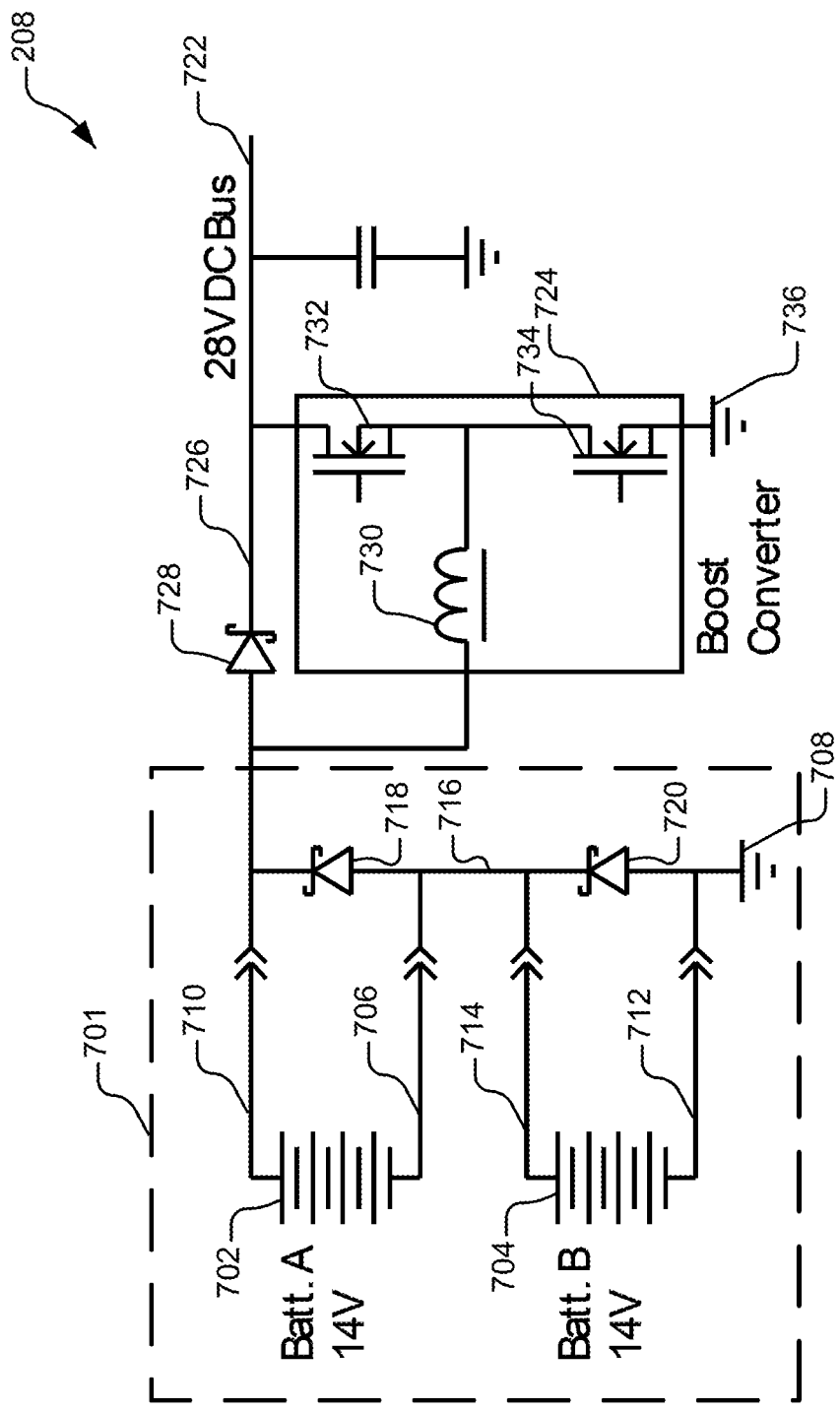
FIG. 7 is schematic illustration of a part of the electrical circuitry of one embodiment of the non-implantable charger.

FIG. 7 is schematic illustration of a part of the electrical circuitry of one embodiment of the non-implantable charger 208. The non-implantable charger 208 can include power features 700 that can include a first energy storage feature 702 and a second energy storage feature 704. The first and second energy storage features 702, 704 can be any components that are capable of storing electric energy including, for example, one or several batteries including one or several rechargeable batteries, one or several capacitors, one or several fuel cells, or the like. The energy storage features 702, 704 can have any desired properties including size, number of cells, voltage, or the like. In some embodiments, the energy storage features 702, 704 can have the same or different features. In some embodiments, for example, the first and second energy storage features 702, 704 can have the same size, voltage, number of cells, or the like, and in some embodiments, the first and second energy storage features 702, 704 can have different sizes, voltages, number of cells, or the like. In the embodiment depicted in FIG. 7, the first and second energy storage features 702, 704 comprise first and second batteries, and specifically first and second rechargeably batteries that each have a voltage of 14 volts.

The first energy storage feature 702 can include a first terminal 706 relatively more proximate to ground 708 in the non-implantable charger 208, and a second terminal 710 relatively more remote from ground 708 in the non-implantable charger 208. Similarly, the second energy storage feature 704 can include a third terminal 712 relatively more proximate to the ground 708 and a fourth terminal 714 relatively more distant from the ground than the third terminal 712.

The first and second energy storage features 702, 704 can, as shown in FIG. 7, be arranged in series. Further, in some embodiments, one or both of the first and second batteries are disconnectable from the non-implantable charger 208. To prevent the opening of the circuit if one or both of the first and second energy storage features 702, 704 is removed and/or fails, the power features 700 include an alternate ground path 716 to which the first and second energy storage features 702, 704 are connected. This alternate ground path 716 can, in some embodiments, include a first flow controller 718, which can be, for example, first diode, located between the first and second terminals 706, 710 of the first energy storage feature 702 and a second flow controller 720, which can be, for example, a second diode, located between the third and fourth terminals 712, 714 of the second energy storage feature 704. The first and second flow controllers 718, 720, can, in some embodiments, be configured to restrict the flow of current to one direction and can provide an electrical connection to ground 708 in the event that one or both of the first and second energy storage features 702, 704 is removed and/or fails.

The non-implantable charger 208 can include a charging bus 722. The charging bus 722 can be used in the powering of the implantable power supply 200, and can specifically receive power from one or both of the first and second energy storage components 702, 704 and provide this power to the implantable power supply 200. The charging bus 722 can have any desired voltage, and in the embodiment of FIG. 7, the charging bus 722 has a voltage of 28 V DC. The charging bus 722 can electrically connect with the power features 700 via one of: a second voltage converter 724; and a second alternate path 726. The second alternate path can include a third flow controller 728 that can be, for example, a third diode. The third flow controller 728 can restrict flow of current to one direction through the second alternate path 726.

The second voltage converter 724 can be any voltage converter that can be configured to controllably receive a first voltage and output a second voltage. In some embodiments, the second voltage converter 724 can be a boost converter that can include a second inductor 730, a third switch 732, which can be, for example, a third transistor, and a fourth switch 734, which can be, for example, a fourth transistor. In some embodiments, the second voltage converter can be used in the event that one of the first and second energy storage features 702, 704 fails and/or is disconnected from the non-implantable charger 208 to maintain the voltage at the charging bus 722 at a desired level. In some embodiments, this voltage can be maintained via the controlling of the third and fourth switches 732, 734 to selectively pass current to the charging bus 722 or to ground 736. In the particular embodiment of FIG. 7 in which each of the first and second energy storage features 702, 704 has a voltage of 14 V DC and in which the charging bus 722 has a voltage of 28 V DC, the second voltage converter 724 can be configured to double the voltage of the remaining one of the first and second energy storage features 702, 704 if the other of the first and second energy storage features 702, 704 is disconnected and/or fails.

In some embodiments, the charging bus 722 can be connected to one or several features configured to transfer power from the non-implantable charger 208 to the implantable power supply 200. In some embodiments, this transfer of power can be performed via one or several physical connections between the non-implantable charger 208 and the implantable power supply 200. These one or several physical connections can include, one or several wires, cables, or the like. In some embodiments, the transfer of power can be accomplished wirelessly via, for example, a coupling such as an inductive coupling. In some such embodiments, the one or several features configured to transfer power from the non-implantable charger 208 to the implantable power supply 200 can include the TETS transmitter 210 which can include a coil such as an inductive coil.

Figure 8:
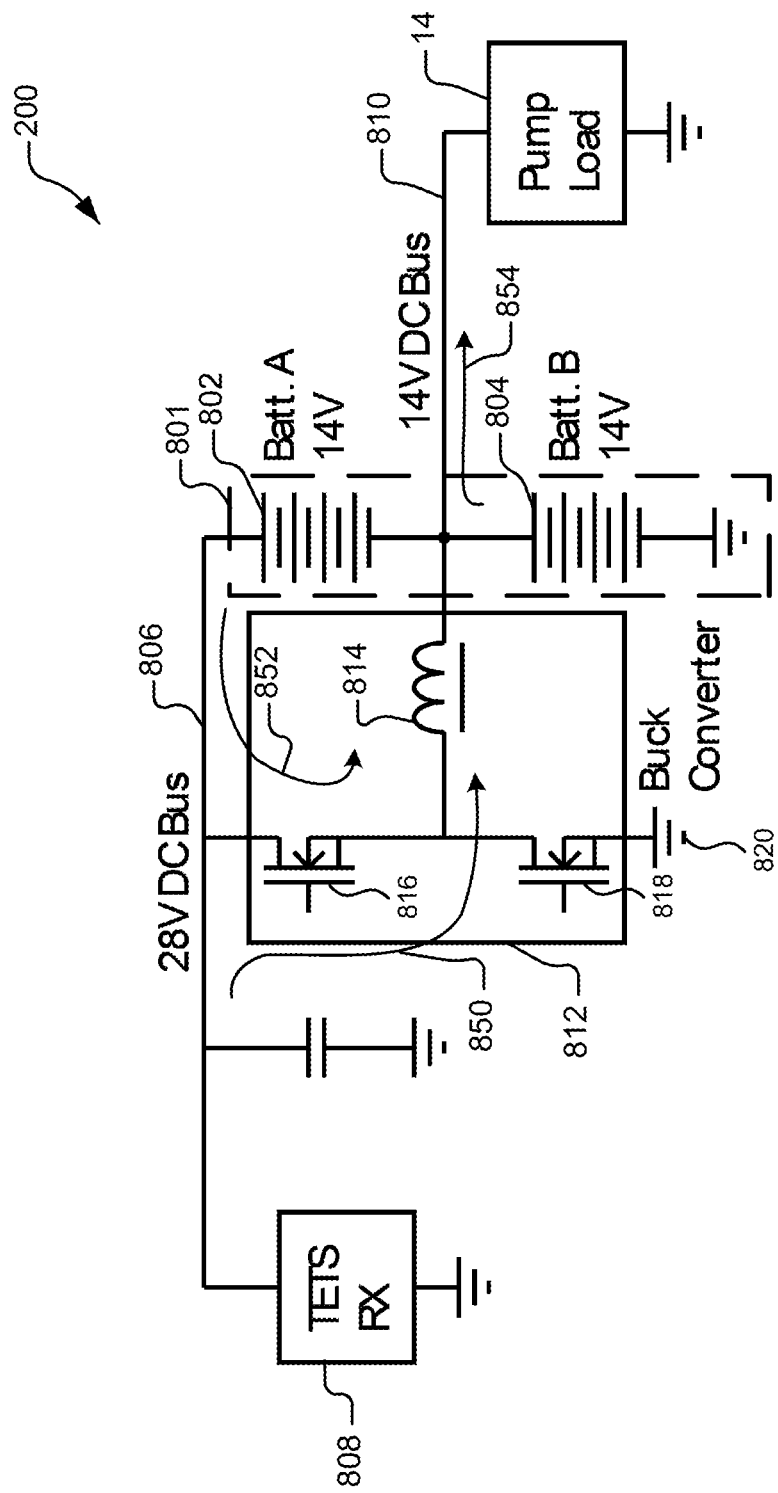
FIG. 8 is schematic illustration of a part of the electrical circuitry of one embodiment of the implantable power supply

FIG. 8 is schematic illustration of a part of the electrical circuitry of one embodiment of the implantable power supply 200. The implantable power supply 200 can include power components 801 that can include a first energy storage component 802 and a second energy storage component 804. The first and second energy storage features 702, 704 can be any components that are capable of storing electric energy including, for example, one or several batteries including one or several rechargeable batteries, one or several capacitors, one or several fuel cells, or the like. The energy storage components 802, 804 can have any desired properties including size, number of cells, voltage, or the like. In some embodiments, the energy storage components 802, 804 can have the same or different features. In some embodiments, for example, the first and second energy storage components 802, 804 can have the same size, voltage, number of cells, or the like, or the first and second energy storage components 802, 804 can have different sizes, voltages, number of cells, or the like. In one embodiment, for example, the first energy storage component 802 can have a first voltage and/or a first number of cells, and the second energy storage component 804 can have a second voltage and/or a second number of cells.

In the embodiment depicted in FIG. 8, the first and second energy storage components 802, 804 comprise first and second batteries, and specifically first and second rechargeable batteries that each have a voltage of 14 volts. In some embodiments, the first and second energy storage components 802, 804 can be arranged in series. The series arrangement of the first and second energy storage components 802, 804 shown in FIG. 8 results in an intermediate voltage of 14 V DC at a node intermediate between the first and second energy storage components 802, 804 and a total voltage of 28 V DC when measured across both the first and second energy storage components 802, 804.

The implantable power supply 200 can further include an input bus 806 that can be electrically connected, and specifically directly electrically connected, to the first energy storage component 802 and to a power source 808. In some embodiments, the power source 808 can be configured to receive power from the non-implantable charger 208. In some embodiments, this power can be received from one or several physical connections between the non-implantable charger 208 and the implantable power supply 200. These one or several physical connections can include, one or several wires, cables, or the like. In some embodiments, this power can be wirelessly received via, for example, a coupling such as an inductive coupling. In some such embodiments, the one or several features configured to receive power from the non-implantable charger 208 at the implantable power supply 200 can include the TETS receiver 206, which can include a coil such as an inductive coil.

In some embodiments, the input bus can be powered by one or both of the power source 808 and the first energy storage component 802. In some embodiments, the voltage of the input bus can match, for example, the total voltage as measured across the series arrangement of the first and second energy storage components 802, 804. This voltage, as depicted in FIG. 8 can be, for example, 28 V DC.

The implantable power supply 200 can further include an output bus 810, and a first voltage converter 812 electrically connecting the input bus 806 and the output bus 810. Further, in some embodiments, the first and second energy storage components 802, 804 can electrically connect to the output bus 810 at the node intermediate between the first and second energy storage components 802, 804. Thus, the second energy storage component 804 can, in some embodiments, power the output bus 810. Further, in embodiments in which the output bus 810 connects to the node intermediate between the first and second energy storage components 802, 804, the output bus 810 can have a second voltage that matches the intermediate voltage at the node between the first and second energy storage components 802, 804. This voltage, as depicted in FIG. 8 can be, for example, 14 V DC, which can, in some embodiments be, half the voltage of the input bus 806.

In some embodiments, the difference between the voltages of the input and output buses 806, 810 can improve the efficiency and functionality of the implantable power supply 200. In some embodiments, the use of the voltage converter 812 to decrease the voltage from the input bus 806 to the voltage of the output bus 810 can improve the efficiency with which power is received at the implantable power supply 200. Specifically, the implantable power supply 200 may, in some embodiments, more efficiently receive power from the non-implantable charger 208 as the voltage of the input bus 806 increases. Thus the use of the voltage converter 812, which can, in some embodiments, increase the size of the implantable power supply 200, can increase the efficiency of the power transfer from the non-implantable charger 208.

The first voltage converter 812 can be any voltage converter that can be configured to controllably receive a first voltage and output a second voltage, and specifically to convert a first voltage to a second voltage. In some embodiments, the first voltage converter 812 can be a buck converter, a flyback converter, or the like. The voltage converter 812 can convert current from a higher voltage at the input bus 806 to current at a lower voltage at the output bus 810. In some embodiments, the buck converter can include a first inductor 814, a first switch 816, which can be, for example, a first transistor, and a second switch 818, which can be, for example, a second transistor. In some embodiments, the first voltage converter 812 can be used to maintain a desired voltage at the output bus 810 and/or supply a desired amount of current to the output bus 810. In some embodiments, this voltage and/or current can be maintained via the controlling of the first and second switches 816, 818 to pass current to the output bus 810, selectively from one of the input bus 806 and ground 820.

In some embodiments, and as shown in FIG. 8, the output bus 810 can be electrically connected to the implantable blood pump 14 such that the output bus 810 can power the implantable blood pump 14. In other words, as the input bus 806 can power the output bus 810 via the first voltage converter 812, in some embodiments, the first voltage converter 812 can output current at the voltage of the output bus 810 to the implantable blood pump 14 and/or can power the implantable blood pump 14.

In some embodiments, the implantable power source 200 can include multiple power pathways, which can be, for example, redundant pathways, through which the implantable blood pump 14 can be powered. Specifically, in some embodiments, the implantable power supply 200 can include a first power pathway 850. In some embodiments, the first power pathway can extend from the power source 808 to the output bus 810 and/or to the implantable blood pump 14 via the input bus 806 and the first voltage converter 812. In some embodiments, the implantable power supply 200 can include a second power pathway 852. The second power pathway 852 can be redundant to the first power pathway 850. In some embodiments, the second power pathway can extend from the first energy storage component 802 to the output bus 810 and/or to the implantable blood pump 14 via the input bus 806 and the first voltage converter 812.

In some embodiments, the implantable power supply 200 can include a third power pathway 854. The third power pathway 854 can be redundant to one or both of the first power pathway 850 and the second power pathway 852. The third power pathway 854 can extend from the second energy storage component 804 to the implantable blood pump 14 via the output bus 810, and can, in some embodiments, exclude one or both of the input bus 806 and the first voltage converter 812.

Alternatively, in some embodiments, the electrical circuitry shown in FIG. 8 can be used in the non-implantable charger 208 instead of the electrical circuitry shown in FIG. 7. In such an embodiment, the electrical circuitry of FIG. 8 would be run in reverse in that the first and second energy storage components 802, 804 would provide power to the input bus 806 either via the first energy storage component 802 or via the voltage converter 812. The input bus 806 would then provide power to the power source 808 which could be a TETS transmitter. The power source 808 would then power the implantable power source 200. In some embodiments in which the electrical circuitry shown in FIG. 8 is used in the non-implantable charger 208, the electrical circuitry does not include the blood pump 14 connected to the output bus 810.

Figure 9:
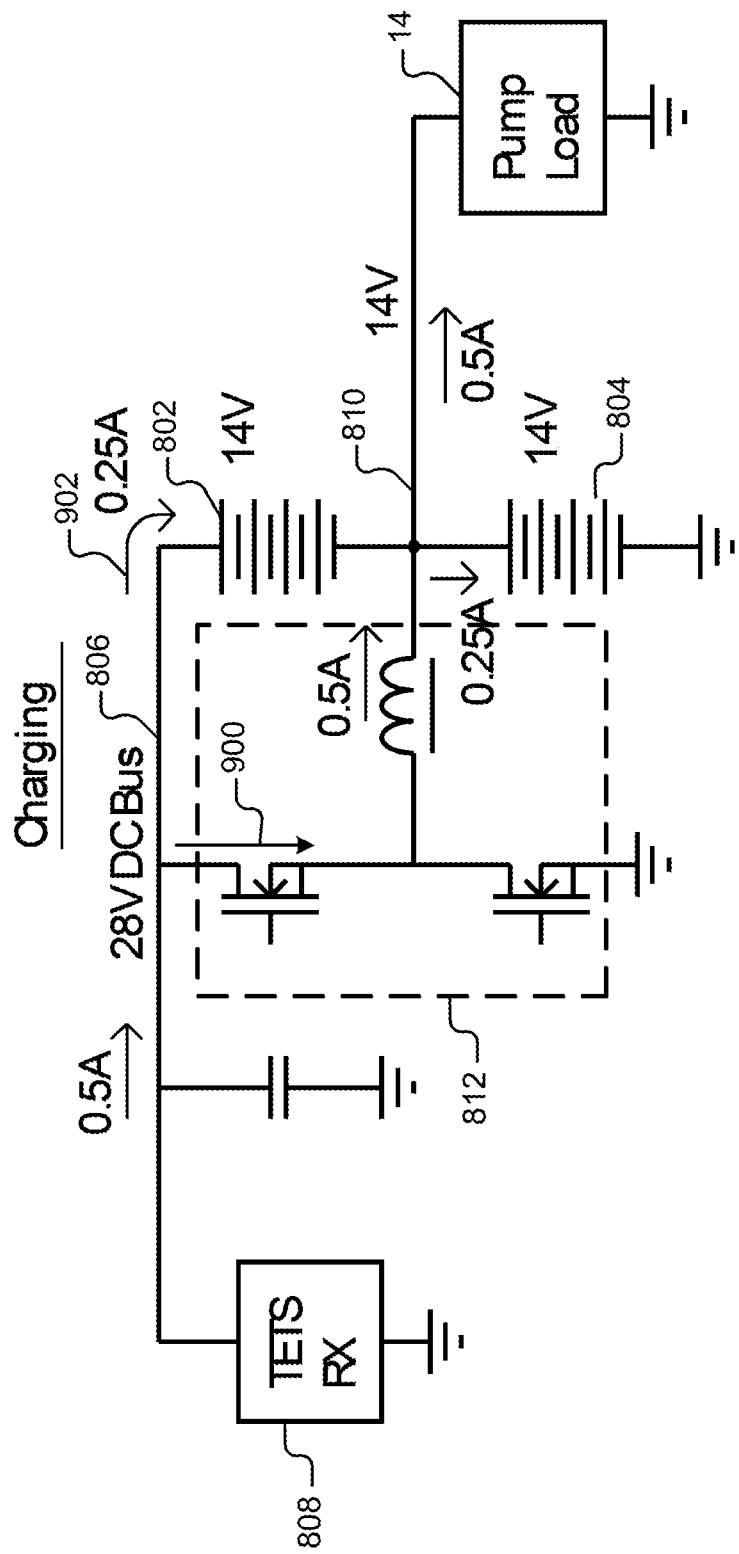
FIG. 9 is a schematic illustration of one embodiment of operation of an implantable power supply in which one or both of first and second energy storage components are charging.
Figure 10:
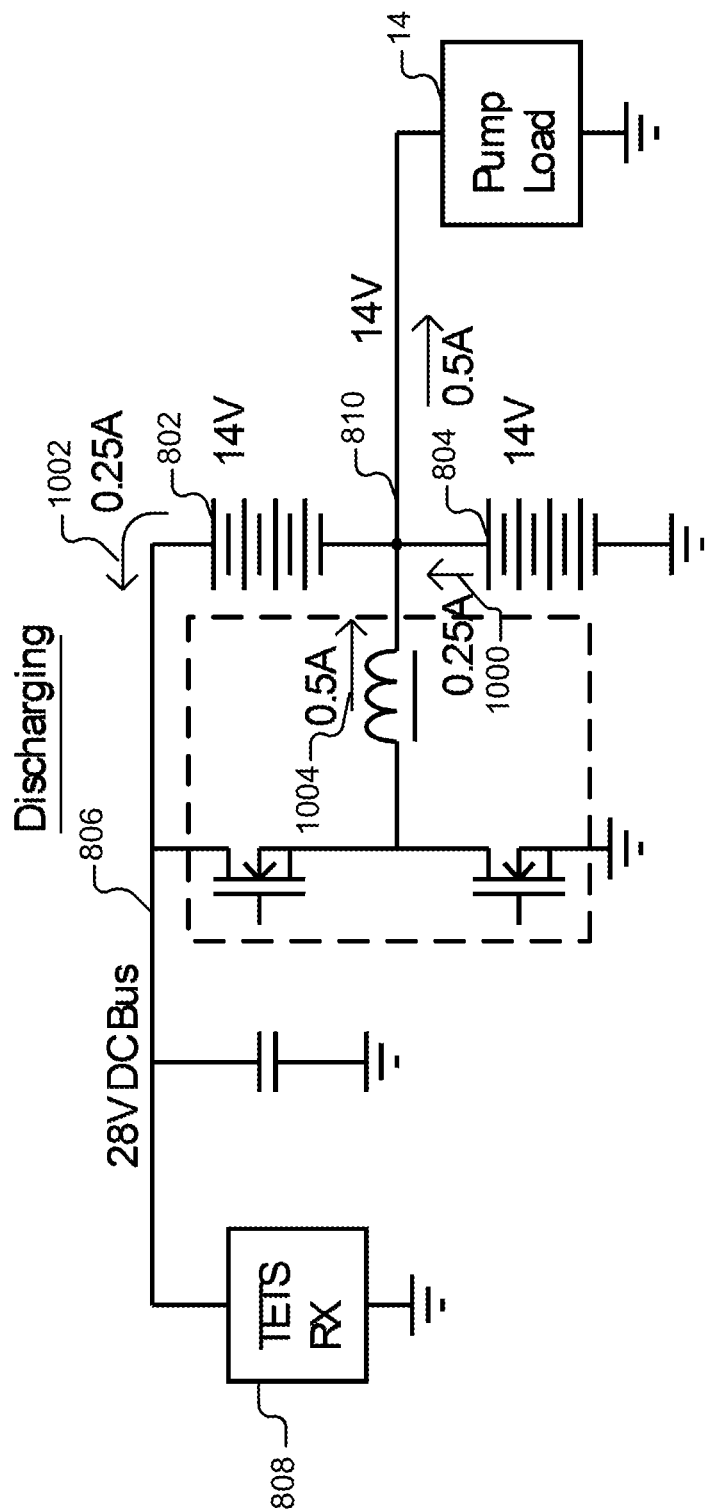
FIG. 10 is a schematic illustration of one embodiment of operation of an implantable power supply in which the first and second energy storage components are discharging.
Figure 11:
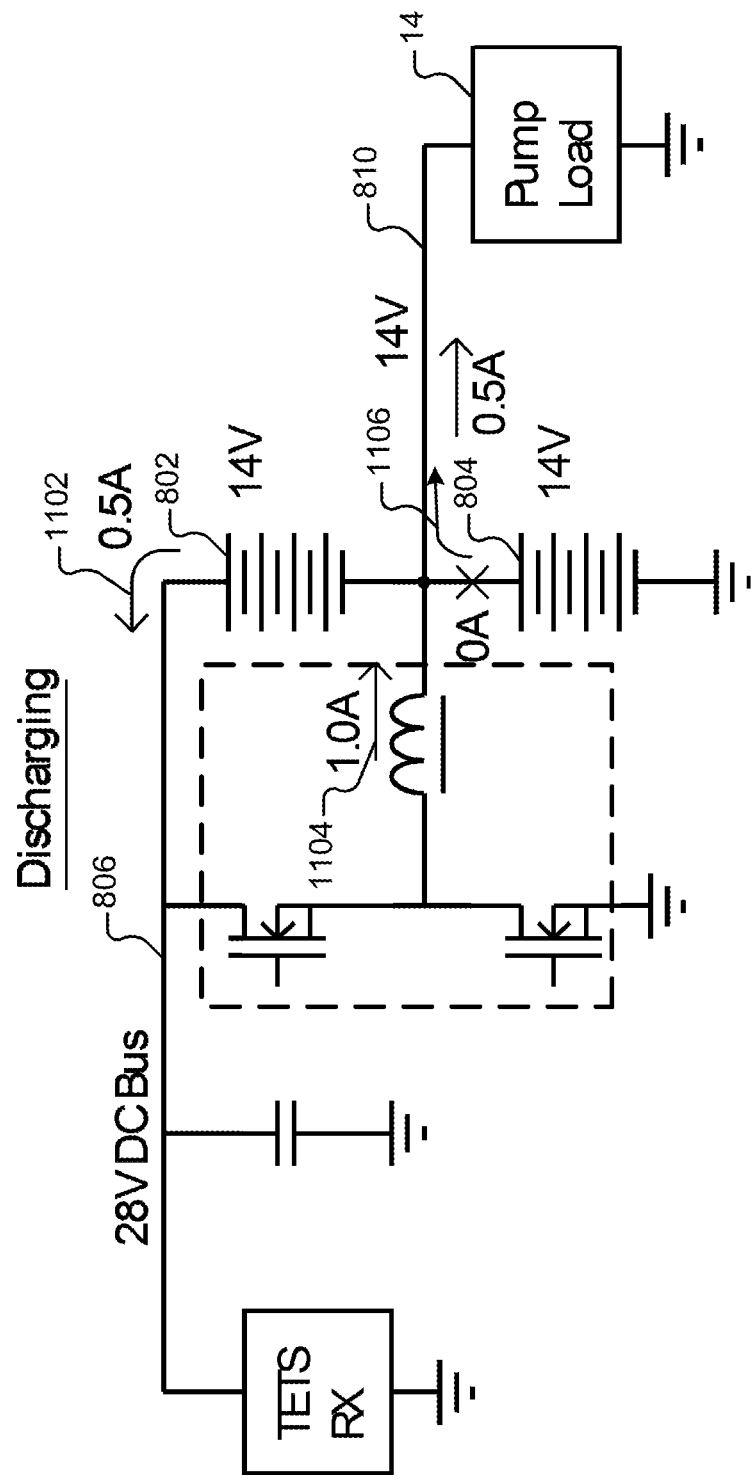
FIG. 11 is a schematic illustration of one embodiment of operation of an implantable power supply in which the first energy storage component is discharging.

FIGS. 9-11 are schematic illustrations of embodiments of the operation of the circuitry of the implantable power supply 200. Specifically, FIG. 9 depicts one embodiment of the operation of the implantable power supply 200 in which the first and second energy storage components 802, 804 are charging. Although FIG. 9 depicts the charging of both the first and second energy storage components 802, 804, it will be appreciated that the first and second energy storage components 802, 804 can also be individually charged.

In FIG. 9, power is received by the power source 808. The power source 808 then powers the output bus 806. The power at the output bus 806 is split between a first portion (indicated by arrow 900) that passes through the voltage converter 812 to power the output bus 810, and a second portion (indicated by arrow 902) that charges the first and second energy storage components 802, 804. The voltage converter 812 converts the voltage of the power from the first voltage corresponding to the voltage of the input bus 806 to the second voltage corresponding to the voltage of the output bus 810. The output bus 810 powers the implantable blood pump.

FIG. 10 depicts one embodiment of the operation of the implantable power supply 200 in which the powering of the power source 808 is inadequate to power the implantable blood pump 14 and/or to charge one or both of the first and second energy storage components 802, 804. Thus, the implantable blood pump 14 is wholly or partially powered by the first and second energy storage components 802, 804.

Specifically, in FIG. 10, power is received from the first and second energy storage components 802, 804 at the input bus 806 as indicated by arrows 1000, 1002. The input bus 806 powers the voltage converter 812 that converts the voltage of the power from the first voltage corresponding to the voltage of the input bus 806 to the second voltage corresponding to the voltage of the output bus 810. The voltage converter 812 powers the output bus 810 as indicated by arrow 1004. The output bus 810 then powers the blood pump 14.

FIG. 11 depicts one embodiment of the operation of the implantable power supply 200 in which the powering of the power source 808 is inadequate to power the implantable blood pump 14 and/or to recharge one or both of the first and second energy storage components 802, 804. Specifically, in the embodiment of FIG. 11, no power is received from the power source 808, and the second energy storage component 804 is likewise not providing any power.

In FIG. 11, power is received from the first energy storage component 802 at the input bus 806 as indicated by arrow 1102. The input bus 806 powers the voltage converter 812 that converts the voltage of the power from the first voltage corresponding to the voltage of the input bus 806 to the second voltage corresponding to the voltage of the output bus 810. The voltage converter 812 powers the output bus 810 as indicated by arrow 1104. The output bus 810 then powers the blood pump 14.

In some embodiments, the power source 808 may provide no power or inadequate power to power the blood pump 14 and the first energy storage component may likewise provide no power or inadequate power to the input bus 806 to power the blood pump 14. In such an embodiment the additional power can come from the second energy storage component 804 and follow a path as indicated by arrow 1106.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of electrically powering an implantable blood pump, the method comprising:
   receiving, by an implanted power source, electrical power from an external charger;
   providing a first power pathway from the implanted power source to the implantable blood pump;
   providing a second power pathway from a first energy storage component to the implantable blood pump, wherein the second power pathway is redundant to the first power pathway;
   providing a third power pathway from a second energy storage component to the implantable blood pump, wherein the third power pathway is redundant to the first power pathway and the second power pathway; and
   powering the implantable blood pump by at least one of the first power pathway, the second power pathway, or the third power pathway.

2. The method of claim 1, wherein the implanted power source receives the electrical power from the external charger transcutaneously.

3. The method of claim 1, wherein the first power pathway comprises at least a portion of an input bus coupled to the implanted power source, and wherein the second power pathway and the third power pathway bypass the input bus.

4. The method of claim 1, wherein the first power pathway and the second power pathway comprise at least a portion of an input bus coupled to the implanted power source.

5. The method of claim 4, wherein the third power pathway bypasses the input bus.

6. The method of claim 1, further comprising:
   receiving, at a first voltage converter, an electrical current from the implanted power source at a first voltage; and
   outputting, by the first voltage converter, the received electrical current at a second voltage suitable for outputting to the implantable blood pump.

7. The method of claim 6, wherein the first power pathway and the second power pathway comprise the first voltage converter, and wherein the third power pathway bypasses the first voltage converter.

8. The method of claim 6, wherein the first power pathway comprises the first voltage converter, and wherein the second power pathway and the third power pathway bypass the first voltage converter.

9. The method of claim 8, wherein the first energy storage component comprises a first battery comprising a first number of cells, and wherein the second energy storage component comprises a second battery comprising a second number of cells.

10. The method of claim 1, further comprising charging, by the implanted power source, the first energy storage component and the second energy storage component via an input bus coupled to the implanted power source.

11. The method of claim 1, wherein the external charger comprises:
   a first energy storage feature;
   a second energy storage feature, wherein the first and second energy storage features are arranged in series; and
   a second voltage converter, wherein the second voltage converter comprises a boost converter configured to double a voltage of at least one of: the first energy storage feature; and the second energy storage feature.

12. A method of electrically powering an implantable blood pump, the method comprising:
   powering an input bus having a first voltage, wherein the input bus is coupled to a power source and a first energy storage component, and wherein the input bus is powered by at least one of: the power source; and the first energy storage component;
   converting the first voltage to a second voltage via a voltage converter, wherein the voltage converter is electrically coupled to the input bus; and
   powering an output bus having the second voltage, wherein the output bus is electrically coupled with the voltage converter and a second energy storage component, wherein the output bus is powered by at least one of the voltage converter and the second energy storage component, and wherein the first and second energy storage components are arranged in series.

13. The method of claim 12, further comprising charging at least one of the first energy storage component and the second energy storage component by the power source via the input bus.

14. The method of claim 12, further comprising discharging at least one of the first energy storage component and the second energy storage component to power the implantable blood pump via the output bus.

15. The method of claim 14, wherein the input bus is only powered by the first energy storage component.

16. The method of claim 14, wherein the powering of the input bus is inadequate to power the implantable blood pump.

17. The method of claim 12, wherein the power source comprises a transcutaneous energy transfer system (TETS) receiver.

18. The method of claim 17, further comprising transmitting power from an external charger to the power source.

19. The method of claim 18, wherein the external charger comprises a TETS transmitter.

20. The method of claim 19, wherein at least one of the TETS receiver and the TETS transmitter comprises an inductive coil.

* * * * *